US010123882B2

(12) United States Patent
Stevenson et al.

(10) Patent No.: US 10,123,882 B2
(45) Date of Patent: Nov. 13, 2018

(54) SPINAL IMPLANT SYSTEM AND METHOD

(71) Applicant: Warsaw Orthopedic, Inc., Warsaw, IN (US)

(72) Inventors: Tyler S. Stevenson, Phoenix, AZ (US); Nicholas M. Benson, Cordova, TN (US); Richard L. Brown, Mesa, AZ (US); Calvert S. Bontemps, Germantown, TN (US); Newton H. Metcalf, Memphis, TN (US); Larry Tyler, Mesa, AZ (US); Kevin T. Foley, Germantown, TN (US); Mark E. Henschel, Phoenix, AZ (US); Michael W. Barror, Gilbert, AZ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 466 days.

(21) Appl. No.: 14/792,256

(22) Filed: Jul. 6, 2015

(65) Prior Publication Data
US 2017/0007420 A1 Jan. 12, 2017

(51) Int. Cl.
*A61F 2/44* (2006.01)
*A61N 1/08* (2006.01)
(Continued)

(52) U.S. Cl.
CPC .............. *A61F 2/447* (2013.01); *A61B 5/076* (2013.01); *A61B 5/4851* (2013.01); *A61F 2/30767* (2013.01); *A61N 1/0551* (2013.01); *A61N 1/08* (2013.01); *A61F 2002/3008* (2013.01); *A61F 2002/30014* (2013.01); *A61F 2002/30052* (2013.01); *A61F 2002/30062* (2013.01); *A61F 2002/30069* (2013.01); *A61F 2002/3082* (2013.01); *A61F 2002/3092* (2013.01); *A61F 2002/3093* (2013.01); *A61F 2002/30125* (2013.01); *A61F 2002/30131* (2013.01); *A61F 2002/30133* (2013.01); *A61F 2002/30156* (2013.01); *A61F 2002/30224* (2013.01); *A61F 2002/30836* (2013.01); *A61F 2002/30841* (2013.01); *A61F 2310/00017* (2013.01); *A61F 2310/00029* (2013.01);
(Continued)

(58) Field of Classification Search
CPC ..................................................... A61F 2/447
See application file for complete search history.

(56) References Cited

U.S. PATENT DOCUMENTS 4,781,591 A 11/1988 Allen
5,383,935 A 1/1995 Shftkhanzadeh
(Continued)

FOREIGN PATENT DOCUMENTS

WO 84-01298 A1 4/1984

OTHER PUBLICATIONS

International Search Report and Written Opinion for PCT/US2016/041135 the counterpart application dated Sep. 12, 2016, 15 pages.

*Primary Examiner* — Olivia C Chang

(57) ABSTRACT

A spinal implant includes an implant body including a first endplate and a second endplate. A plurality of electrodes include at least one electrode disposed with the first endplate and at least one electrode disposed with the second endplate such that the electrodes conduct an electric current to stimulate tissue growth adjacent the implant body. Systems, surgical instruments and methods are disclosed.

17 Claims, 12 Drawing Sheets

(51) Int. Cl.
    *A61N 1/05*    (2006.01)
    *A61F 2/30*    (2006.01)
    *A61B 5/07*    (2006.01)
    *A61B 5/00*    (2006.01)

(52) U.S. Cl.
    CPC ............ *A61F 2310/00077* (2013.01); *A61F 2310/00113* (2013.01); *A61F 2310/00155* (2013.01); *A61F 2310/00173* (2013.01); *A61F 2310/00293* (2013.01); *A61F 2310/00329* (2013.01); *A61F 2310/00359* (2013.01); *A61F 2310/00365* (2013.01); *A61F 2310/00407* (2013.01); *A61N 2001/083* (2013.01)

(56) References Cited

U.S. PATENT DOCUMENTS

| | | | |
|---|---|---|---|
| 6,120,502 A * | 9/2000 | Michelson | A61B 17/1671 606/247 |
| 6,292,699 B1 | 9/2001 | Simon et al. | |
| 7,455,672 B2 | 11/2008 | Michelson | |
| 8,147,549 B2 | 4/2012 | Metcalf, Jr. et al. | |
| 8,494,644 B2 | 7/2013 | Cowan et al. | |
| 8,838,249 B2 | 9/2014 | Nycz | |
| 2011/0118852 A1 | 5/2011 | Evans | |
| 2014/0114382 A1 | 4/2014 | Kim | |
| 2015/0190242 A1 * | 7/2015 | Blain | A61F 2/30771 623/17.12 |
| 2016/0270927 A1 * | 9/2016 | Zellmer | A61F 2/4455 |

* cited by examiner

SPINAL IMPLANT SYSTEM AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative disc disease, disc herniation, osteoporosis, spondylolisthesis, stenosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, partial or complete discectomy, corpectomy and laminectomy, and implantable prosthetics. As part of these surgical treatments, spinal constructs, such as, for example, bone fasteners, spinal rods and interbody devices can be used to provide stability to a treated region. For example, during surgical treatment, interbody implants can be delivered to a surgical site for fixation with bone to immobilize a joint. Such interbody implants can include bone growth promoting material to enhance fixation of the interbody implants with the bone. This disclosure describes an improvement over these technologies.

SUMMARY

In one embodiment, a spinal implant is provided. The spinal implant includes an implant body including a first endplate and a second endplate. A plurality of electrodes include at least one electrode disposed with the first endplate and at least one electrode disposed with the second endplate such that the electrodes conduct an electric current to stimulate tissue growth adjacent the implant body. In some embodiments, systems, surgical instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
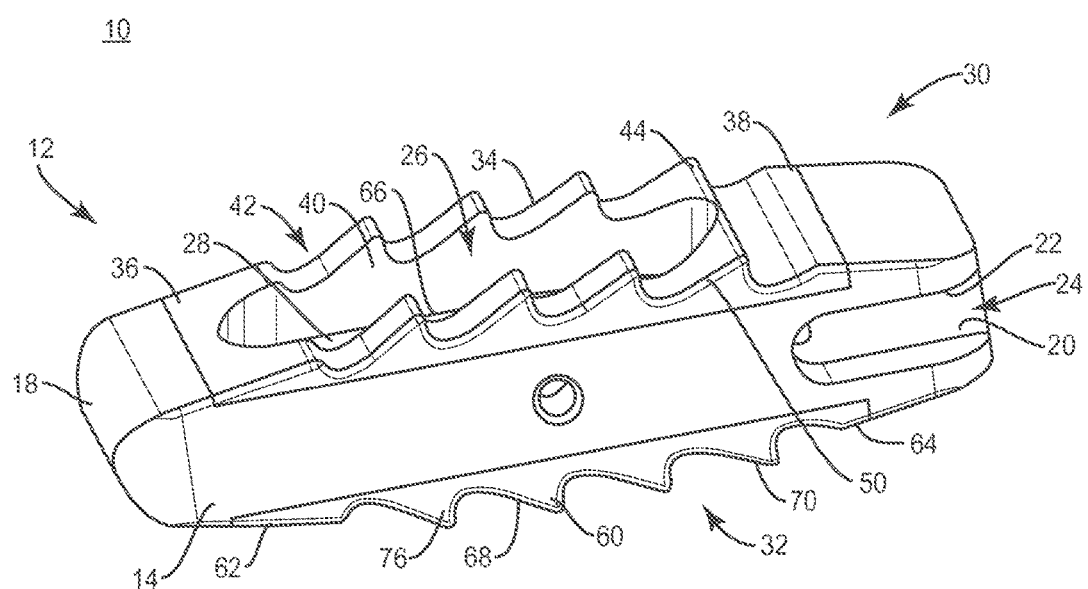
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system including a spinal implant and a method for treating a spine. In some embodiments, the surgical systems and methods of the present disclosure are employed with a spinal joint fusion, for example, with a cervical, thoracic, lumbar and/or sacral region of a spine.

In some embodiments, the surgical system includes an implant, such as, for example, an interbody implant. In some embodiments, the interbody implant includes a bone growth stimulation interbody device. In some embodiments, the interbody implant includes an electronic bone growth stimulator enabled interbody cage. In some embodiments, the interbody implant includes a titanium coating on a superior surface and a titanium coating on an inferior surface. In some embodiments, the interbody implant includes anodes and cathodes to generate a selected electric field in and around the interbody implant to facilitate selective stimulation of bone growth around and through the interbody implant. In some embodiments, the anodes and cathodes can be embedded, snapped and/or coated with one or more surfaces of the interbody implant. In some embodiments, the interbody implant includes sidewall-embedded anode and cathode windows. In some embodiments, the interbody implant includes titanium coated endplate electrodes. In some embodiments, the interbody implant includes sidewall-embedded anode and cathode windows and titanium coated endplate electrodes.

In some embodiments, the surgical system includes an interbody implant including electronic components that generate an electric current to stimulate bone growth. In some embodiments, the electronic components include diagnostics that provide diagnostic feedback and/or measure at least one diagnostic condition. In some embodiments, the diagnostics include, for example, embedded sensors for strain, stress and/or temperature. In some embodiments, the electronic components include remote power options using telemetry, such as, for example, near-field communication (NFC). In some embodiments, the electronic components include coils located outside a patient for powering the electronic components. In some embodiments, the electronic components include a NFC power harvesting integrated circuit. In some embodiments, the electronic components include an analog front end integrated circuit. In some embodiments, the electronic components include a microprocessor integrated circuit.

In some embodiments, the surgical system includes an interbody implant including electronic components that generate an electric field adjacent to and encompass a selected region of spinal tissue to stimulate bone growth. In some embodiments, the electronic components include one or more electrodes disposed in a configuration to generate an electric field over a selected region of spinal tissue to stimulate bone growth. In some embodiments, the electronic components include two electrodes configured to generate an elliptical electric field over a selected region of spinal tissue to stimulate bone growth. In some embodiments, the electronic components include one or more external devices, such as, for example, a tablet, computer and/or healthcare database that remotely communicate, such as, wireless technology, NFC technology and/or the transmission/reception of radio-frequency (RF) signals with the interbody implant. In some embodiments, the electronic components include micro-electronic systems, which may include micro-electronic substrates, a leadless stimulator placed in the interbody implant, and/or a hermetically sealed pressure sensor. In some embodiments, the electronic components include titanium cathode and anode windows placed in an interbody implant for galvanic current and/or galvanic coupling across a graft space. In some embodiments, the electronic components include titanium cathode and anode time release windows placed in an interbody implant for galvanic current and/or galvanic coupling across a graft space, radiopaque markers and a polyetheretherketone (PEEK) cage body.

In some embodiments, the surgical system includes an interbody implant including integration of electronic components into the interbody implant to monitor patient's recovery and may include an accelerometer, temperature sensor, strain gauge and/or a magnetometer. In some embodiments, the interbody implant includes electrical bone growth stimulation by implanting an interbody implant with a small circuit and an electrode; the circuit being powered from an external device via telemetry (NFC, for example). In some embodiments, the interbody implant generates electrical currents across an interior of a fusion cage by a galvanic cell built directly into cage material (PEEK) and the cell is created by using dissimilar metals on either side of the cage. In some embodiments, the interbody implant comprises a bio-absorbable or partially bio-absorbable bone growth stimulator. In some embodiments, the interbody implant stimulates bone growth and comprises multiple porous cathodes.

In some embodiments, the surgical system includes an interbody implant with electronic components having variable power settings. In some embodiments, the surgical system includes an interbody implant with electronic components that sense or detect impedance and/or collect impedance measurements as a proxy/indicator of fusion. In some embodiments, the surgical system includes an interbody implant with electronic components that take diagnostic measurements from onboard sensors of an interbody cage. In some embodiments, the electronic components monitor diagnostic measurements of impedance or interpreting such impedance measurements as an indication of bone growth/fusion through/onto/around the interbody implant.

In some embodiments, the surgical system includes an interbody implant comprising a PEEK interbody fusion cage having an electrical bone growth stimulator with increased fusion rates by applying an electrical stimulation across two electrodes in an area where fusion of a spine is desired. In some embodiments, the electrical stimulation creates an electric field which, in some embodiments, due to the piezo-resistive nature of bone tissue, causes a mechanical load across the bone. In some embodiments, the bone responds to the load with growth. In some embodiments, the interbody implant is molded over or otherwise encapsulates electronic components into the interbody implant. In some embodiments, the interbody implant provides a small, localized electric stimulation to promote bone growth while also maintaining the cavity in the cage to maximize the amount of graft/tissue packed into the interbody implant. In some embodiments, the interbody implant includes titanium coated endcaps such as the electrodes. In some embodiments, the interbody implant includes electronics, electrodes, and an interbody cage that is contained within an interbody space. In some embodiments, the interbody implant includes diagnostics that take an impedance measurement across the electrodes and use that measurement to determine if/how well bone has begun to grow or fused across the interbody implant. In some embodiments, the interbody implant includes electronic components having an impedance measurement circuit to provide interrogable impedance measurements indicative of the growth of bone through the interbody implant.

In some embodiments, the surgical system includes an interbody implant that is implanted and comprises a serial configuration, cross section and/or layered configuration, upon implantation with tissue, which includes bone, titanium endplate, PEEK cage, titanium endplate and bone with interstitial fluid flowing about the contacts. In some embodiments, the surgical system includes stages of treatment such that as bone growth begins, an increase in blood vessels at the interfaces occurs and bony tissue across the interbody implant is generated. In some embodiments, these stages of treatment can include a detectable diagnostic that is detected with an impedance measurement. In some embodiments, this configuration allows a surgeon to request information from the interbody implant relating to the status of the fusion without needing medical imaging, such as, x-ray or magnetic resonance imaging (MRI).

In some embodiments, the surgical system includes an interbody implant comprising a PEEK interbody cage defining a central cavity and an electrode that extends into the central cavity; the electrode maintaining electrical isolation. In some embodiments, the interbody cage includes a titanium coating. In some embodiments, the electrode includes an anode electrode that is isolated from a cathode electrode, and the cathode electrode is isolated from the anode electrode. In some embodiments, the electrode comprises a frame that supports and/or is supported by the interbody cage. In some embodiments, the interbody implant includes extended electrodes that bend around the sides of the interbody implant, for example, extending upward and downward from the endplates of the interbody implant.

In some embodiments, the surgical system includes an interbody implant that stimulates bony tissue with an electric potential and causes bone to grow. In some embodiments, the interbody implant includes a titanium coating in a cavity thereof and bony tissue growing into the cavity can be stimulated directly across bone graft packed into the cavity, thereby creating an electric potential across the region adjacent to and including the bone graft packed interbody cage for achieving a bone growth/fusion.

In some embodiments, the surgical system includes printed circuit board assembly inserts including up to two or three individual boards. In some embodiments, the individual boards are connected together in a desired shape before molding a PEEK mold over the electronic assembly. In some embodiments, the surgical system includes titanium snap on endplates. In some embodiments, the present system is configured to accommodate various implant sizes.

In some embodiments, the surgical system includes a single electronic assembly that is connected by a flexible material, such as, for example, a flex circuit. In some embodiments, the flex circuit facilitates manufacture and the molding process of an interbody implant.

In some embodiments, the surgical system includes two series coils per side. In some embodiments, the surgical system provides an increased connection between circuit boards. In some embodiments, the present system includes a locking feature configured to secure the circuit boards to the endcaps.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, unless specifically referred to otherwise. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, silver alloys, copper alloys, gold alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including PEEK, polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as conductivity, insulation and/or electrical isolation, strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce implants, such as, for example, an interbody implant, at a surgical site within a subject body of a patient, which includes, for example, a spine. In some embodiments, the implant can include spinal constructs including one or more bone fasteners, spinal rods, connectors and/or plates. In some embodiments, spinal implant system 10 includes one or a plurality of selected implants for a particular surgical procedure. In some embodiments, spinal implant system 10 includes one or a plurality of implants selectively personalized to a patient.

Spinal implant system 10 comprises a spinal implant, such as, for example, an interbody implant 12. Interbody implant 12 includes an implant body, such as, for example, an interbody cage 14. Cage 14 extends between an end, such as, for example, a leading end 18 and an end, such as, for example, an insertion end 20. End 18 includes a surface having a blunt tip to prevent interbody implant 12 from damaging surrounding tissue and/or nerves during insertion. End 20 includes a surface 22 that defines a cavity 24 configured for engagement with a surgical instrument, such as, for example, an insertion tool (not shown).

In some embodiments, cage 14 includes dimensions, such as, for example, a width, a thickness and/or a height, and a length. In some embodiments, cage 14 can be selected having selected dimensions based on one or more criteria, as described herein. In some embodiments, one or more dimensions of cage 14 are determined and selected based on a footprint of a selected anatomy, such as, for example, endplate surfaces of adjacent vertebrae having intervertebral disc tissue removed therebetween. In some embodiments, cage 14 is molded, during a manufacturing and/or fabrication method for producing interbody implant 12, with electronic components, as described herein, of interbody implant 12. In some embodiments, cage 14 is molded with an insert, such as, for example, a printed circuit board assembly 80 described herein. In some embodiments, cage 14 is molded with printed circuit board assembly 80 and electrodes, such as, for example, endcaps 34, 60, as described herein. In some embodiments, interbody implant 12 includes electronic components disposed in a selected configuration and PEEK material is molded with, on or about the electronic components to form cage 14 and/or to encapsulate the electronic components with interbody implant 12.

In some embodiments, the cross-section geometry of interbody implant 12 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, interbody implant 12 includes an opening 26, which includes an opening 40 of an endplate 30, an opening 28 of cage 14 and an opening 66 of an endplate 32, as described herein, configured to receive an agent, which may include bone graft (not shown) and/or other materials, as described herein, for employment in a fixation or fusion treatment, as described herein. In some embodiments, the agent may include therapeutic polynucleotides or polypeptides and bone growth promoting material, which can be packed or otherwise disposed on or about the surfaces of the components of spinal implant system 10, including interbody implant 12. In some embodiments, cage 14 includes an interconnected porous configuration, which facilitates bone ingrowth. In some embodiments, cage 14 includes one or a plurality of layers. In some embodiments, tissue, interstitial tissue and/or fluids may be disposed with opening 26.

Endplate 30 includes an electrode, such as, for example, an endcap 34, which comprises an anode electrode of electronic components and/or circuitry of spinal implant system 10 that is connected with interbody implant 12. Endcap 34 extends between an end 36 and an end 38. End 36 is configured for engagement with end 18, as described herein. End 38 is configured for engagement with end 20, as described herein. Endcap 34 includes opening 40 in communication with openings 28, 66, and is configured to receive an agent, which may include bone graft (not shown) and/or other materials for employment in a fixation or fusion treatment, as described herein.

Endcap 34 defines a portion of a superior surface, such as, for example, a vertebral engaging surface 42 of endplate 30. In some embodiments, surface 42 includes one or a plurality of tissue penetrating members, such as, for example, teeth 44. In some embodiments, one or more teeth 44 may have various configurations, for example, round, oval, rectangular, polygonal, irregular, tapered, offset, staggered, uniform and non-uniform. In some embodiments, surface 42 may be rough, textured, porous, semi-porous, dimpled, knurled, grooved and/or polished to facilitate engagement with vertebral tissue. In some embodiments, the vertebral tissue may include intervertebral tissue, endplate surfaces and/or cortical bone.

Endcap 34 includes a surface 46 configured to mate with cage 14 and/or circuit board assembly 80. In some embodiments, surface 46 includes one or a plurality of mating elements configured for mating engagement with cage 14, as described herein. In some embodiments, the mating elements may be disposed at alternate orientations, relative to surface 46, such as, for example, perpendicular, transverse, and/or other angular orientations such as acute or obtuse, coaxial and/or may be offset or staggered. In some embodiments, surface 46 may include a mating element surface that can be rough, textured, porous, semi-porous, dimpled, knurled, toothed, grooved and/or polished to facilitate mating engagement with cage 14. In some embodiments, the mating element can include clips, key/keyslot, barbs, retaining tracks/slots and/or adhesive.

Endcap 34 includes an electrically conductive material, such as, for example, a coating 50. In some embodiments, coating 50 is fabricated from titanium. In some embodiments, the electrically conductive material of endcap 34 may be fabricated from various materials, such as, for example, metals as described herein, electrolytes, superconductors, semi-conductors, plasmas and non-metallic conductors such as graphite and conductive polymers.

Direct electric current is supplied to coating 50, as described herein, and coating 50 is configured to conduct electric current through tissue, an agent, interstitial tissue and/or fluids disposed adjacent cage 14 and/or within opening 26. Endcap 34 conducts the electric current through cage 14 and to an endcap 60, as described herein, in a configuration to generate a selected electric field in, around, about, through and/or adjacent to interbody implant 12 to selectively stimulate bone growth in, around, about, through and/or adjacent interbody implant 12. In some embodiments, endcap 34 is electrically coupled to cage 14. In some embodiments, endcap 34 is electrically insulated from cage 14. In some embodiments, all or a portion of endcap 34 is fabricated from a conductive material, such as, for example, titanium, which may be solid, porous, semi-porous and/or heterogeneous with another material. In some embodiments, endcap 34 may be removably attached to cage 14 or may be permanently affixed to cage 14. In some embodiments, endcap 34 includes a titanium snap-on endplate.

Endplate 32 includes an electrode, such as, for example, an endcap 60, which comprises a cathode electrode of electronic components and/or circuitry of spinal implant system 10 that is connected with interbody implant 12. Endcap 60 extends between an end 62 and an end 64. Endcap 60 is spaced apart from endcap 34 in a configuration to conduct direct electric current through tissue, an agent, interstitial tissue and/or fluids disposed adjacent cage 14 and/or within opening 26, as described herein. End 62 is configured for engagement with end 18, as described herein. End 64 is configured for engagement with end 20, as described herein. Endcap 60 includes opening 66 in communication with openings 28, 40 and is configured to receive an agent, which may include bone graft (not shown) and/or other materials for employment in a fixation or fusion treatment, as described herein.

Endcap 60 defines a portion of an inferior surface, such as, for example, a vertebral engaging surface 68 of endplate 32. In some embodiments, surface 68 includes one or a plurality of tissue penetrating members, such as, for example, teeth 70. In one embodiment, one or more teeth 70 may have various configurations, for example, round, oval, rectangular, polygonal, irregular, tapered, offset, staggered, uniform and non-uniform. In some embodiments, surface 68 may be rough, textured, porous, semi-porous, dimpled, knurled, grooved and/or polished to facilitate engagement with vertebral tissue. In some embodiments, the vertebral tissue may include intervertebral tissue, endplate surfaces and/or cortical bone.

Endcap 60 includes a surface 72 configured to mate with cage 14 and/or circuit board assembly 80. In some embodiments, surface 72 includes one or a plurality of mating elements configured for mating engagement with cage 14, as described herein. In some embodiments, the mating elements may be disposed at alternate orientations, relative to surface 72, such as, for example, perpendicular, transverse, and/or other angular orientations such as acute or obtuse, coaxial and/or may be offset or staggered. In some embodiments, surface 72 may include a mating element surface that can be rough, textured, porous, semi-porous, dimpled, knurled, toothed, grooved and/or polished to facilitate mating engagement with cage 14. In some embodiments, the mating element can include clips, key/keyslot, barbs, retaining tracks/slots and/or adhesive.

Endcap 60 includes an electrically conductive material, such as, for example, a coating 76. In some embodiments, coating 76 is fabricated from titanium. In some embodiments, the electrically conductive material of endcap 60 may be fabricated from various materials, such as, for example, metals as described herein, electrolytes, superconductors, semi-conductors, plasmas and non-metallic conductors such as graphite and conductive polymers.

Figure 4:
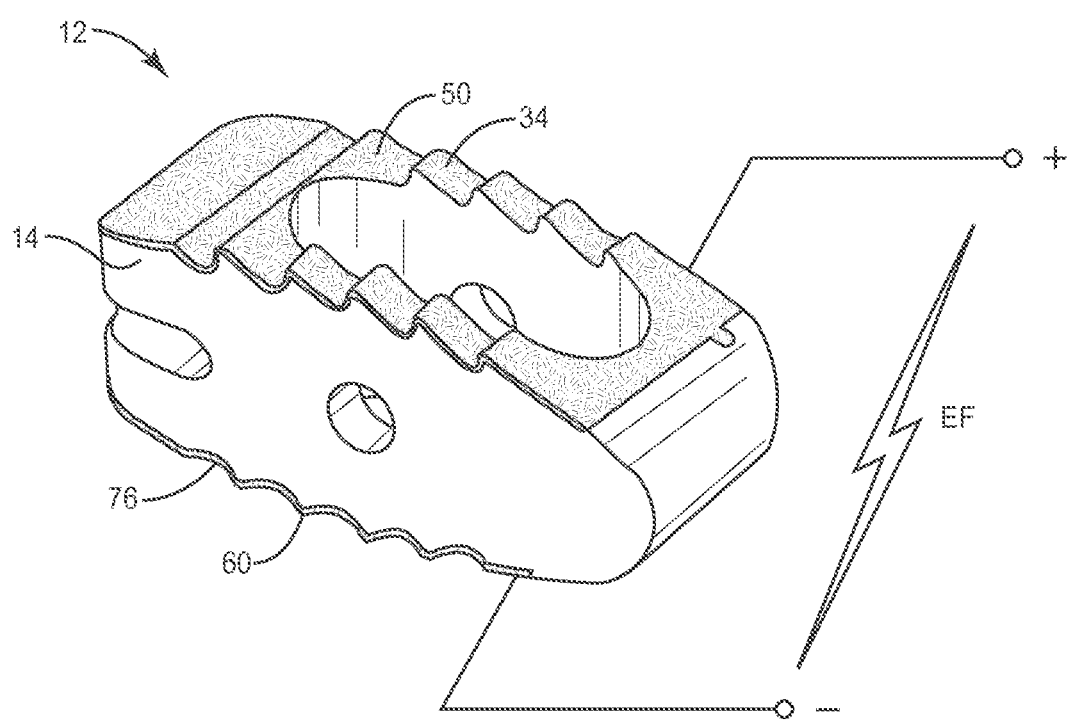
FIG. 4 is a perspective view of components of one embodiment of a surgical system in accordance with the principles of the present disclosure.
Figure 5:
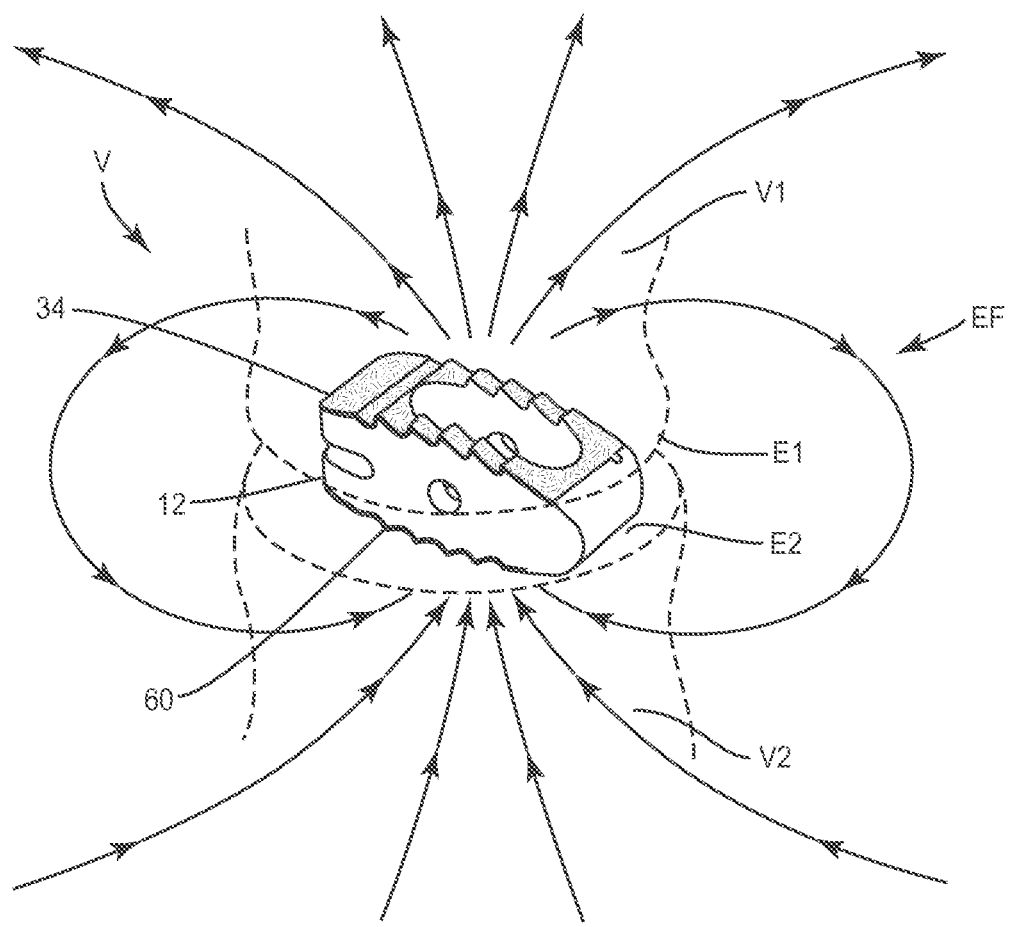
FIG. 5 is a perspective view of components of one embodiment of a surgical system in accordance with the principles of the present disclosure disposed with vertebrae.
Figure 6:
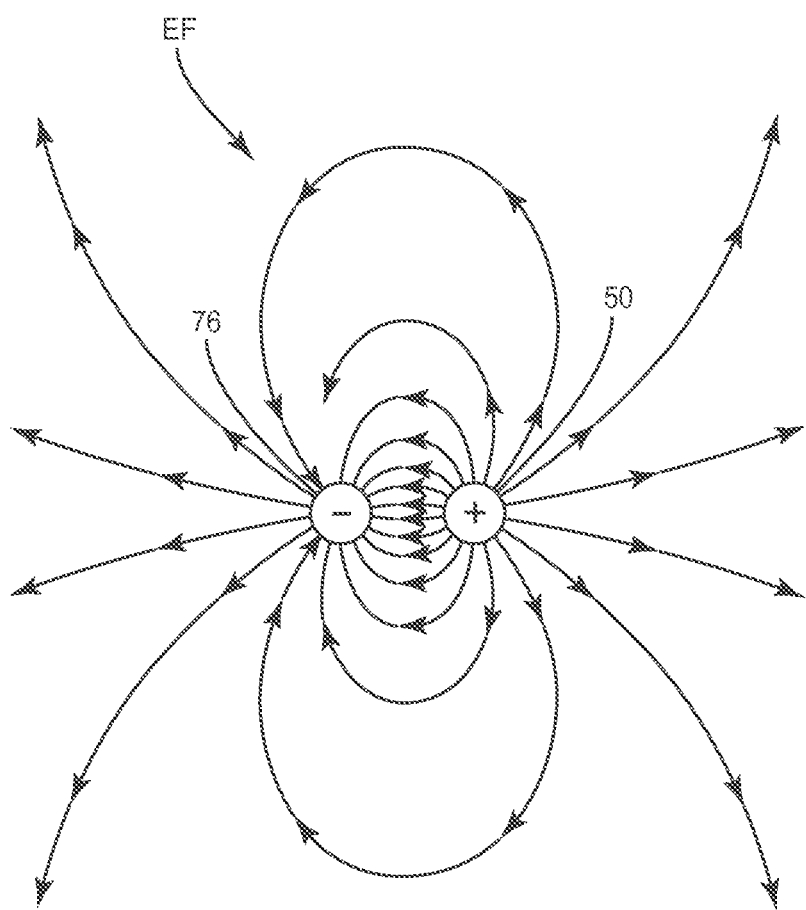
FIG. 6 is a schematic illustration of components of one embodiment of a surgical system in accordance with the principles of the present disclosure.

Coating 76 is configured to conduct direct electric current through tissue, an agent, interstitial tissue and/or fluids disposed adjacent cage 14 and/or within opening 26. Endcap 60 conducts the electric current through cage 14 and from endcap 34, as described herein, in a galvanic coupling to generate a selected electric field EF, as shown in FIG. 4, in, around, about, through and/or adjacent to interbody implant 12 to selectively stimulate bone growth in, around, about, through and/or adjacent interbody implant 12. Coating 50 comprises an anode electrode and coating 76 comprises a cathode electrode, which are selectively configured with cage 14 to generate an elliptical electric field EF, as shown in FIGS. 5 and 6, in, around, about, through and/or adjacent to interbody implant 12 to selectively stimulate bone growth in, around, about, through and/or adjacent interbody implant 12.

Figure 7:
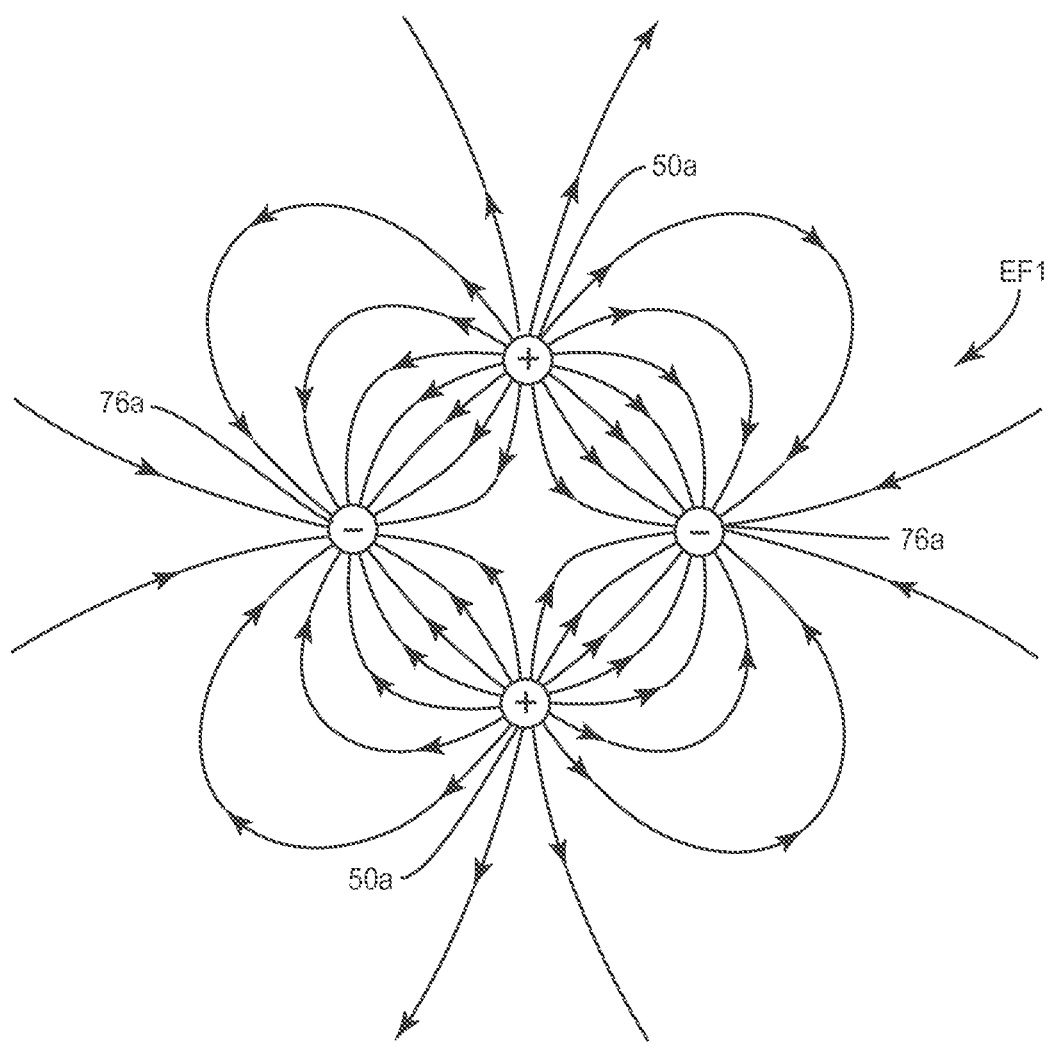
FIG. 7 is a schematic illustration of components of one embodiment of a surgical system in accordance with the principles of the present disclosure.

In some embodiments, the endplate electrodes of interbody implant 12 are selectively configured with cage 14 to generate a selected electric field in, around, about, through and/or adjacent to interbody implant 12 to selectively stimulate tissue growth in, around, about, through and/or adjacent to interbody implant 12. In one embodiment, as shown in FIG. 7, interbody implant 12 includes a plurality of anode electrodes 50a and a plurality of cathode electrodes 76a that are selectively configured with cage 14 to generate a selectively configured electric field EF1 in, around, about, through and/or adjacent to interbody implant 12 to selectively stimulate bone growth in, around, about, through and/or adjacent interbody implant 12.

In some embodiments, endcap 60 is electrically coupled to cage 14. In some embodiments, endcap 60 is electrically insulated from cage 14 and/or endcap 34. In some embodiments, all or a portion of endcap 60 is fabricated from a conductive material, such as, for example, titanium, which may be solid, porous, semi-porous and/or heterogeneous with another material. In some embodiments, endcap 60 may be removably attached to cage 14 or may be permanently affixed to cage 14. In some embodiments, endcap 60 includes a titanium snap-on endplate. In some embodiments, endcap 60 may comprise one or a plurality of electrodes and endcap 34 may comprise one or a plurality of electrodes. In some embodiments, endcap 60 may comprise one or a plurality of anode electrodes and endcap 34 may comprise one or a plurality of cathode electrodes. In some embodiments, the endplate electrodes of interbody implant 12 can comprise endplates 30, 32 both being shorted together as cathodes and interbody implant 12 further including a third electrode that operates as an anode to both endplate cathodes.

Figure 2:
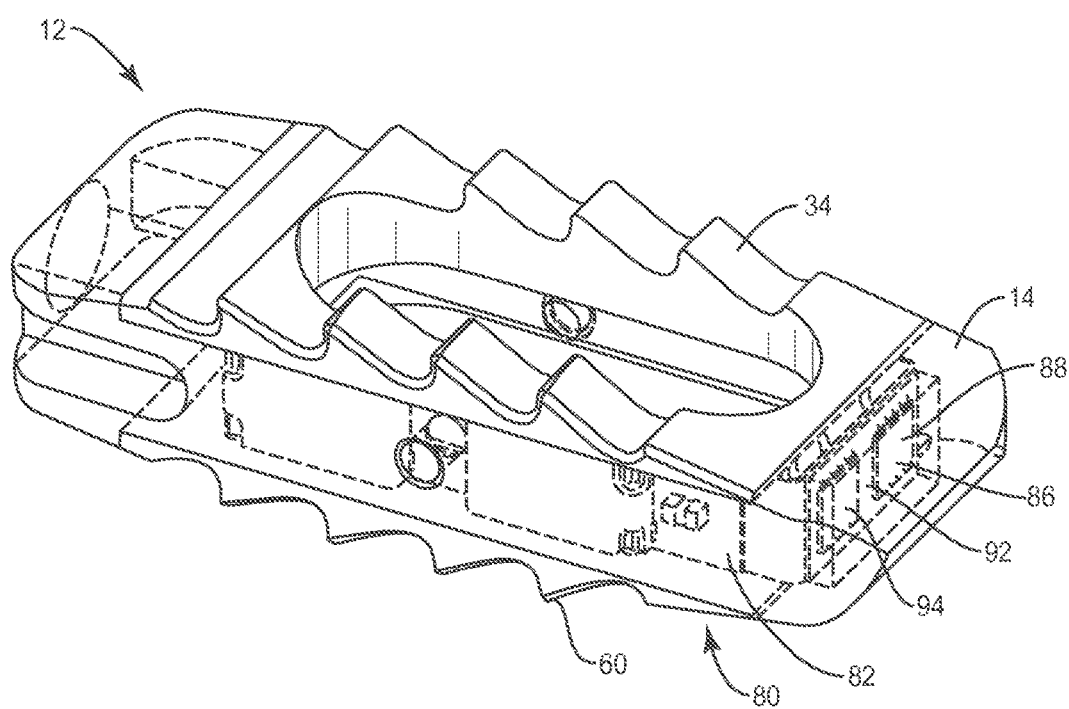
FIG. 2 is a cutaway perspective view of the components shown in FIG. 1.
Figure 3:
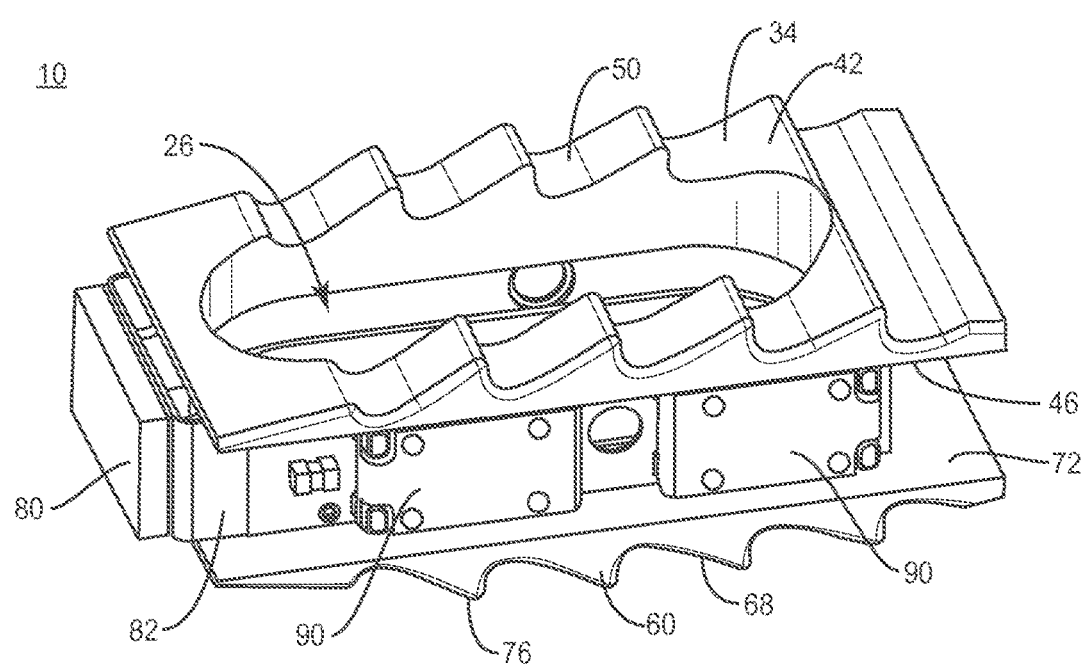
FIG. 3 is perspective view of the components of the surgical system shown in FIG. 1.

Interbody implant 12 includes electronic components, such as, for example, a printed circuit board assembly 80, as shown in FIGS. 2 and 3, which includes one or more components for delivering electric current to the electrodes, powering interbody implant 12 and/or detecting/sensing diagnostics, and is suitable for implantation.

Circuit board assembly 80 includes a non-conductive component, such as, for example, a substrate 82. Substrate 82 is connected with conductive circuitry and/or coils configured to conduct a current to endcap 34 and/or endcap 60 to generate electric field EF adjacent interbody implant 12 to selectively stimulate tissue growth adjacent cage 14. In some embodiments, circuit board assembly 80 is a flexible printed circuit. In some embodiments, substrate 82 includes conductive pads and other features etched from conductive metal sheets and laminated onto substrate 82.

Substrate 82 is connected with and/or includes circuitry and one or more integrated circuits or micro-electronic chips for delivering electric current to the electrodes, powering interbody implant 12 and/or detecting/sensing diagnostics. In some embodiments, the one or more integrated circuits disposed with circuit board assembly 80 can remotely communicate with electronic components of spinal implant system 10 disposed outside or external to a body of a patient. In some embodiments, circuit board assembly 80 can remotely communicate with such external electronic components to power interbody implant 12 and/or transfer, transmit and/or receive data relating to interbody implant 12 including treatment and/or diagnostics, as described herein. In some embodiments, the remote communication can include a wireless link, such as, for example, Bluetooth, NFC, WiFi, MICS, and/or as described in U.S. Pat. No. 5,683,432 "Adaptive Performance-Optimizing Communication System for Communicating with an Implantable Medical Device" to Goedeke, et al., the contents of which being hereby incorporated by reference in its entirety.

Figure 8:
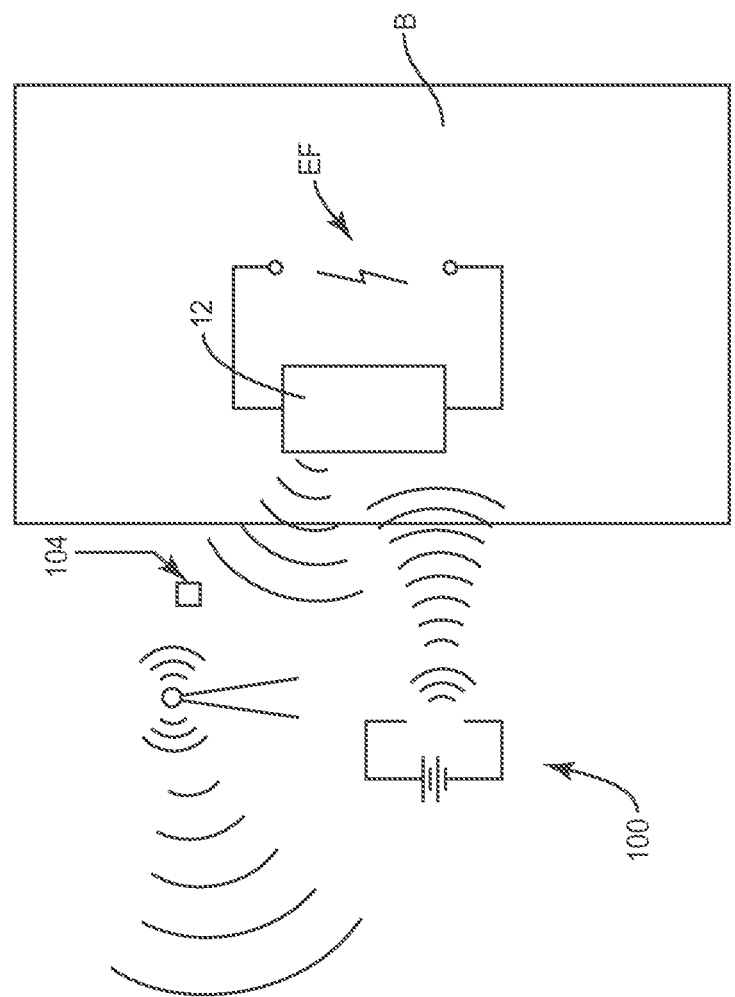
FIG. 8 is a plan view of components of one embodiment of a surgical system in accordance with the principles of the present disclosure.

For example, in some embodiments, spinal implant system 10 includes a remote power source 100 disposed outside or external to a body B of a patient and circuit board assembly 80 includes a NFC integrated circuit device 86 for powering interbody implant 12 and conducting electric current through endcaps 34, 60, as shown in FIG. 8. NFC device 86, as shown in FIG. 2, is configured for inductive communication with remote power source 100 for power harvesting of a communication signal for powering interbody implant 12. NFC device 86 may comprise various commercially available integrated circuit devices, see, for example, but not limited to, the RF430 microcontroller distributed by Texas Instruments RF430. In some embodiments, remote power source 100 includes a computer, cell phone, PDA, laptop, surgical instrument, clothing, accessory such as a belt, bag, wallet, pocketbook, backpack or other device mounted with body B, which includes electronic components for communicating with NFC device 86, as described herein. In some embodiments, NFC device 86 operates and/or communicates with remote power source 100 within a radio frequency band of 13.56 MHz, with a bandwidth of approximately 2 MHz.

NFC device 86 employs magnetic induction with, for example, a reader, such as, for example, interbody implant 12 and power source 100. NFC device 86 includes a power harvesting integrated circuit 88 that enables interbody implant 12 to establish radio communication at a short distance to supply power to charge circuit board assembly 80. Substrate 82 includes a magnetic receiving antenna, such as, for example, a plurality of antenna 90 disposed in series. In some embodiments, antenna 90 includes coils and/or solenoids. Antenna 90 is connected with NFC device 86 to convert nearby magnetic fields into energy such that endcaps 34, 60 conduct electric current to selectively stimulate tissue growth adjacent cage 14, as described herein.

Power source 100 emits a small electric current to create a magnetic field that bridges the physical space between power source 100 and interbody implant 12 implanted within body B. NFC device 86 is electrically connected with electronic components of circuit board assembly 80 to charge circuit board assembly 80 disposed with interbody implant 12 by power source 100 disposed external relative to body B. Power source 100 radiates energy through a cutaneous barrier, such as, for example, the skin of body B to adjacent interbody implant 12. An electromagnetic field is generated by a transmitting coil within power source 100 to transmit power across the skin to plurality of antenna 90 disposed with interbody implant 12. The plurality of antenna 90 transfer the received power to interbody implant 12 for charging/powering.

In some embodiments, as shown in FIG. 8, NFC device 86 remotely communicates with a device, such as, for example, a computer 102 that is disposed outside or external to body B to transfer, transmit and/or receive data relating to interbody implant 12 including treatment and/or diagnostic information obtained from interbody implant 12. Interbody implant 12 includes diagnostic sensor electronics 92 connected with one or more sensors disposed about cage 14 and/or endplates 30, 32 and an analog integrated circuit device 94 connected with diagnostic sensor electronics 92 and NFC device 86 to obtain and store data received from interbody implant 12 and surrounding tissue. Diagnostic sensor electronics 92 may comprise various commercially available integrated circuit devices, see, for example, but not limited to, the AD5933 Impedance Converter Network Analyzer distributed by Analog Devices. Integrated circuit device 94 may comprise various commercially available integrated circuit devices, see, for example, but not limited to, the RF430 microcontroller distributed by Texas Instruments RF430.

In some embodiments, diagnostic sensor electronics 92 and/or analog device 94 gather information, such as, for example, loading information, pressure information, tension information, motion information, alignment or misalignment information and/or temperature, relating to interbody implant 12 and/or treatment, as described herein. Computer 102 remotely communicates with NFC device 86, as described herein, to collect data from interbody implant 12 via diagnostic sensor electronics 92. In some embodiments, a reader 104 is disposed on body B that communicates with computer 102. In some embodiments, power source 100, as described herein, includes reader 104. Reader 104 emits a small electric current that creates a magnetic field to bridge the physical space between reader 104 and interbody implant 12. The electric field is received by NFC device 86 and converted into electrical impulses to communicate data and diagnostics, relating to interbody implant 12 and/or treatment to computer 102, as described herein.

Diagnostic sensor electronics 92 provides feedback and/or measures one or more diagnostic conditions. In some embodiments, the diagnostics include, for example, embedded sensors for strain, stress and/or temperature. Diagnostic sensor electronics 92 sense and transmit to computer 102 various diagnostic indicia, and in some embodiments, diagnose and respond to such measurements, such as, for example, in the context of a spinal implant surgery. In some embodiments, a surgeon can monitor a patient after surgery, and make adjustments to interbody implant 12 and/or treatment to avoid a subsequent surgery. In some embodiments, this configuration allows interbody implant 12 and/or treatment to be corrected or modified based on changes that take place subsequent to surgery, and/or for selected and remote changes to diagnostic conditions inside body B. In some embodiments, diagnostic sensor electronics 92 indicate fusion rate of interbody implant 12 with vertebrae.

In some embodiments, diagnostic sensor electronics 92 sense or detect impedance and/or collect impedance measurements as a proxy/indicator of fusion based on configuration of tissue. In some embodiments, diagnostic sensor electronics 92 monitor diagnostic measurements of impedance or interpreting such impedance measurements as an indication of bone growth/fusion in, around, about, through and/or adjacent to interbody implant 12. For example, in some embodiments, diagnostic sensor electronics 92 sense or detect impedance and/or collect impedance measurements based on the configuration of tissue such as fat, muscle, bone and blood.

In some embodiments, diagnostic sensor electronics 92 sense or detect impedance of fat tissue in a range of 2500 through 5000 ohms. In some embodiments, diagnostic sensor electronics 92 sense or detect impedance of transverse muscle in a range of 700 through 2500 ohms. In some embodiments, diagnostic sensor electronics 92 sense or detect impedance of long muscle in a range of 125 through 350 ohms. In some embodiments, diagnostic sensor electronics 92 sense or detect impedance of bone in a range of 1500 through 10000 ohms. In some embodiments, diagnostic sensor electronics 92 sense or detect impedance of blood in a range of 140 through 240 ohms. In one example, interbody implant 12 selectively stimulates bone growth and diagnostic sensor electronics 92 sense a detectable diagnostic of tissue adjacent interbody implant 12 that detects an impedance measurement of 200 ohms corresponding to blood and an impedance measurement of 5000 ohms corresponding to bone.

In some embodiments, the components of interbody implant 12 can be selected for a particular surgical procedure and/or from alternate components of a spinal implant kit based on one or more criteria. In some embodiments, the one or more criteria include, for example, anatomical parameters, implant parameters and/or surgical procedure parameters, as described herein. In some embodiments, the anatomical parameters can include condition, quality, configuration and/or dimension of selected anatomy, for example, one or more disc space dimensions, disc height, disc tissue, and/or one or more vertebra dimensions, vertebra/vertebrae height and/or vertebral tissue, and/or a footprint associated with vertebral tissue including vertebrae and intervertebral discs. In some embodiments, the footprint can include the area defined by vertebral tissue, such as, for example, an endplate surface of one or more vertebra.

In some embodiments, the implant parameters can include predetermined and/or preselected implant size, predetermined and/or preselected implant height, predetermined and/or preselected footprint, targeted implant size, targeted implant height, targeted footprint and/or materials. In some embodiments, the surgical procedure parameters can include one or a plurality of vertebra, uni-lateral treatment, bi-lateral treatment, PLIF, TLIF, DLIF, ACDF, OLIF and/or ALIF. In some embodiments, the components of interbody implant 12 can be selected prior to surgery. For example, a surgeon can conduct imaging diagnosis and/or pre-operative planning using medical imaging, as described herein, to measure anatomical parameters employed to determine implant parameters. In some embodiments, one or more members can be selected for assembly of a personalized interbody implant 12 with predetermined footprint size and target height based on implant footprint size.

In assembly, operation and use, as shown in FIGS. 5 and 8, spinal implant system 10, similar to the systems and methods described herein, is disposed with tissue, such as, for example, vertebrae V of a patient body B for treatment of a spinal disorder, such as those described herein, affecting a section of a spine of a patient. Spinal implant system 10 may also be employed with other surgical procedures.

To treat the affected section of vertebrae V, such as, for example vertebrae V1 and vertebra V2, an incision is made with a surgical instrument, such as, for example, a scalpel (not shown). In some embodiments, a discectomy is performed adjacent the intervertebral space between endplates E1, E2 of adjacent vertebrae V1, V2, as shown in FIG. 5. In some embodiments, sequential trial implants are delivered and used to distract the intervertebral space and apply appropriate tension in the intervertebral space allowing for indirect decompression. In some embodiments, the footprint of interbody implant 12 is selected after trialing.

An inserter (not shown) is connected with interbody implant 12 to direct interbody implant 12 between vertebrae V1, V2 such that surface 42 is disposed with endplate E1 and surface 68 is disposed with endplate E2. The inserter delivers interbody implant 12 through the incision to the surgical site for implantation into the intervertebral space between vertebrae V1, V2 such that interbody implant 12 is disposed with vertebrae V1, V2 for treatment of a spinal disorder. In some embodiments, interbody implant 12 is visualized by fluoroscopy and oriented before malleting into the intervertebral space.

Electrical stimulation across the anode and cathode electrodes, such as, for example, endcaps 34, 60 facilitates fusion of interbody implant 12 with bone tissue of vertebrae V1, V2. Endcaps 34, 60, generate electric field EF adjacent interbody implant 12 to selectively stimulate tissue growth adjacent cage 14 and within opening 26, as described herein. Direct electric current is supplied to endcaps 34, 60, as described herein, to conduct electric current through tissue, an agent, interstitial tissue and/or fluids disposed adjacent cage 14 and/or within opening 26.

Endcap 34 conducts the electric current through cage 14 and to endcap 60, as described herein, in a configuration to generate a selected electric field in, around, about, through and/or adjacent to interbody implant 12 to selectively stimulate bone growth in, around, about, through and/or adjacent interbody implant 12. In some embodiments, the stimulation causes a mechanical load across the bone, tissue, agents, interstitial tissue and/or fluids and the bone and tissue responds to the load with bone growth to facilitate fusion. Diagnostic sensor electronics 92 provide feedback and/or measure diagnostic conditions of the vertebrae. Diagnostic sensor electronics 92 sense and transmit to computer 102 various diagnostic indicia, and also diagnoses and responds to such measurements, such as, for example, in the context of a spinal implant surgery, a surgeon can monitor a patient after or during surgery, and make adjustments to interbody implant 12 or treatment, as described herein.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT, MRI or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 9:
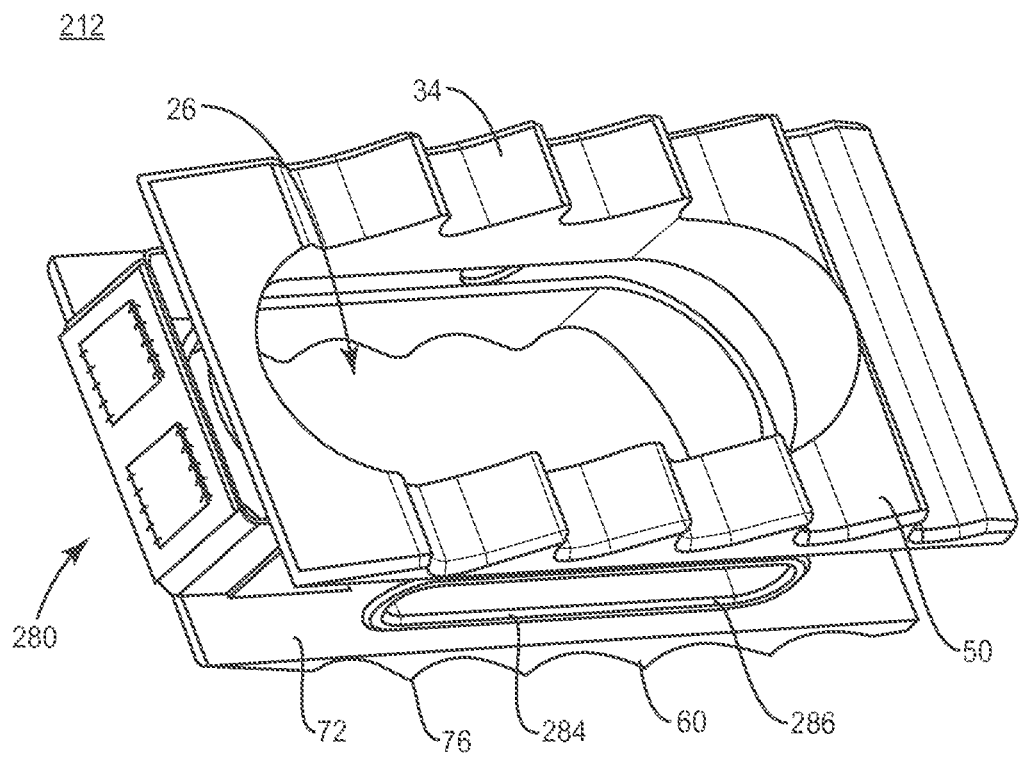
FIG. 9 is perspective view of components of one embodiment of a surgical system in accordance with the principles of the present disclosure.
Figure 10:
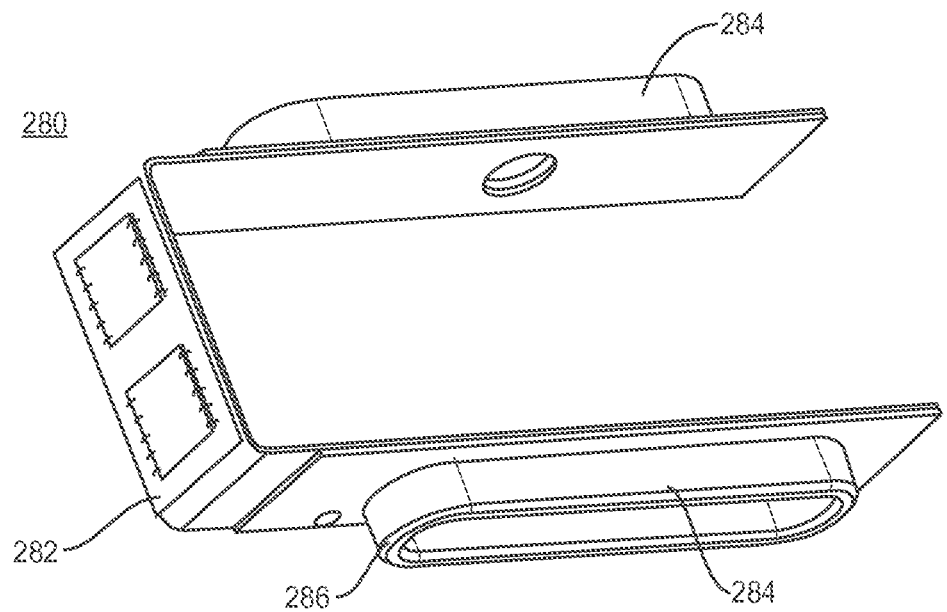
FIG. 10 is perspective view of components of the surgical system shown in FIG. 9.

In one embodiment, as shown in FIGS. 9 and 10, surgical system 10, similar to the systems and methods described herein, includes an interbody implant 212, similar to interbody implant 12 described herein, including endcaps 34, 60 and cage 14, as described herein. Interbody implant 212 includes electronic components, such as, for example, a printed circuit board assembly 280.

Circuit board assembly 280 includes a single electronic assembly that is connected by a flexible material, such as, for example, a flex circuit 282. Circuit 282 is connected with conductive circuitry and/or coils configured to conduct a current to endcap 34 and/or endcap 60 to generate an electric field, as described herein, adjacent interbody implant 212 to selectively stimulate tissue growth adjacent cage 14, as described herein.

Circuit 282 is connected with and/or includes circuitry and one or more integrated circuits or micro-electronic chips for delivering electric current to the electrodes, powering interbody implant 212 and/or detecting/sensing diagnostics, similar to that described herein. The integrated circuits disposed with circuit board assembly 280 can remotely communicate with electronic components of spinal implant system 10 disposed outside or external to a body of a patient, similar to that described herein.

Circuit board assembly 280 includes a NFC integrated circuit device, similar to NFC device 86 described herein, for powering interbody implant 212 and conducting electric current through endcaps 34, 60. Circuit 282 includes a magnetic receiving antennae 284 that each include oblong circular or oval coils 286 disposed on either side of flex circuit 282. Antenna 284 is connected with the NFC device of circuit board assembly 280 to convert nearby magnetic fields into energy such that endcaps 34, 60 conduct electric current to selectively stimulate tissue growth adjacent cage 14, similar to that described herein.

The NFC device of circuit board assembly 280 remotely communicates with a computer, similar to computer 102 described herein, which is disposed outside or external to body B to transfer, transmit and/or receive data relating to interbody implant 212 including treatment and/or diagnostic information obtained from interbody implant 212. Interbody implant 212 includes diagnostic sensor electronics, similar to diagnostic sensor electronics 92 described herein, connected with one or more sensors disposed about cage 14 and/or endplates 30, 32 and an analog microprocessor integrated circuit device, similar to analog microprocessor integrated circuit device 94 described herein, disposed with circuit 282 and connected with the diagnostic sensor electronics and the NFC device of circuit board assembly 280 to obtain and store data received from interbody implant 212 and surrounding tissue. In some embodiments, flex circuit 282 facilitates molding of the electronic components of interbody implant 212 with cage 14. In some embodiments, flex circuit 282 is configured for assembling electronic circuits by mounting electronic devices on a flexible plastic substrate, such as, for example, polyimide, PEEK or transparent conductive polyester film. In some embodiments, flex circuit 282 is manufactured using components used for rigid printed circuit boards, allowing the board to conform to a desired shape, or to flex during its use.

Figure 11:
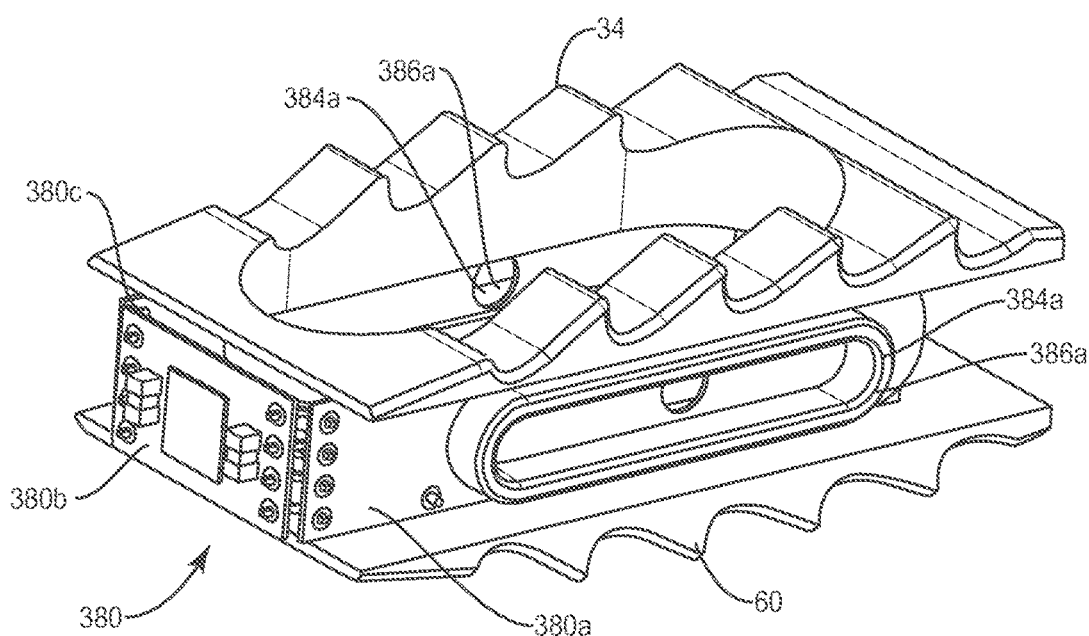
FIG. 11 is perspective view of components of one embodiment of a surgical system in accordance with the principles of the present disclosure.

In one embodiment, as shown in FIG. 11, surgical system 10, similar to the systems and methods described herein, includes an interbody implant 312, similar to interbody implant 12 described herein. Interbody implant 312 includes electronic components, such as, for example, a printed circuit board assembly 380. Circuit board assembly 380 includes multiple boards, such as, for example, boards 380a, 380b and 380c. Boards 380a, 380b and 380c are connected together to facilitate forming various configurations prior to molding cage 14 over endcaps 34, 60 and circuit board assembly 380. In some embodiments, boards 380a, 380b and 380c facilitate the formation of various sizes of interbody implants 312.

Boards 380a, 380b and 380c are connected with conductive circuitry and/or coils configured to conduct a current to endcap 34 and/or endcap 60 to generate an electric field, as described herein, adjacent interbody implant 312 to selectively stimulate tissue growth adjacent cage 14, as described herein.

Boards 380a, 380b and 380c are connected with and/or include circuitry and one or more integrated circuits or micro-electronic chips for delivering electric current to the electrodes, powering interbody implant 312 and/or detecting/sensing diagnostics, similar to that described herein. The integrated circuits disposed with circuit board assembly 380 can remotely communicate with electronic components of spinal implant system 10 disposed outside or external to a body of a patient, similar to that described herein.

Circuit board assembly 380 includes a NFC integrated circuit device, similar to NFC device 86 described herein, for powering interbody implant 312 and conducting electric current through endcaps 34, 60. Boards 380a, 380c each include magnetic receiving antennae 384a that each include oblong circular or oval coils 386a disposed on boards 380a, 380c, respectively. Antennae 384a is connected with the NFC device of circuit board assembly 380 to convert nearby magnetic fields into energy such that endcaps 34, 60 conduct electric current to selectively stimulate tissue growth adjacent cage 14, similar to that described herein.

The NFC device of circuit board assembly 380 remotely communicates with a computer, similar to computer 102 described herein, which is disposed outside or external to body B to transfer, transmit and/or receive data relating to interbody implant 312 including treatment and/or diagnostic information obtained from interbody implant 312. Interbody implant 312 includes diagnostic sensor electronics, similar to diagnostic sensor electronics 92 described herein, connected with one or more sensors disposed about cage 14 and/or endplates 30, 32 and an analog microprocessor integrated circuit device, similar to analog microprocessor integrated circuit device 94 described herein, disposed with boards 380a, 380b and 380c and connected with the diagnostic sensor electronics and the NFC device of circuit board assembly 380 to obtain and store data received from interbody implant 312 and surrounding tissue.

Figure 12:
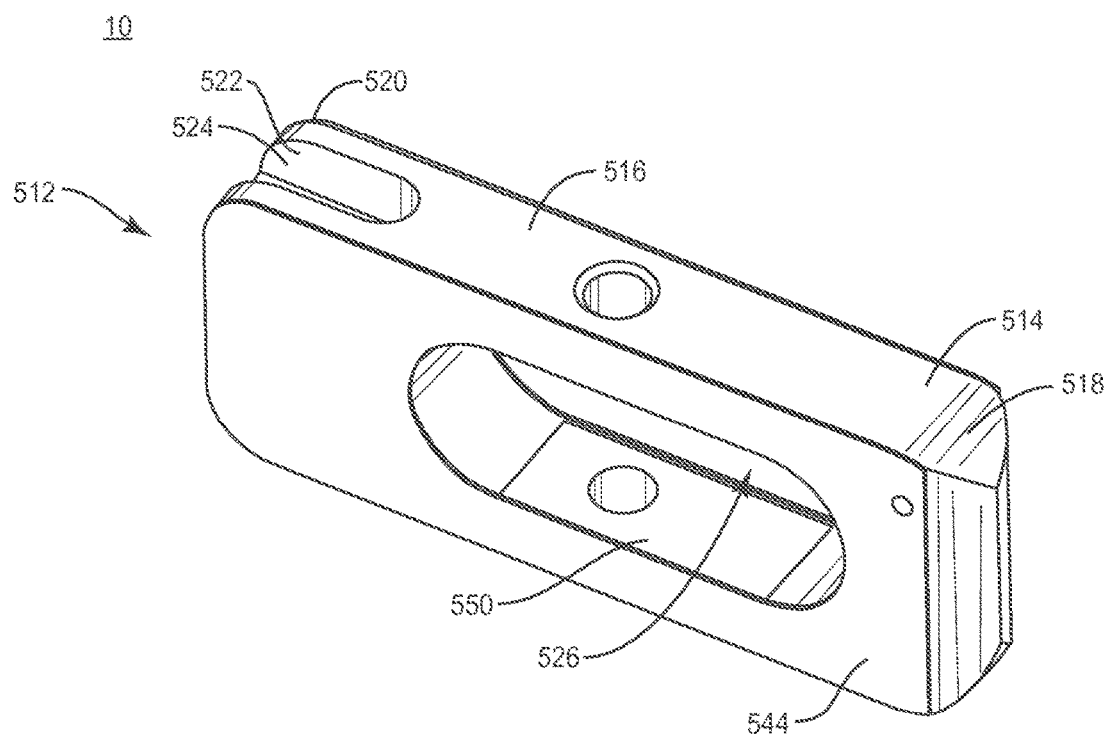
FIG. 12 is a perspective view of components of one embodiment of a surgical system in accordance with the principles of the present disclosure.
Figure 13:
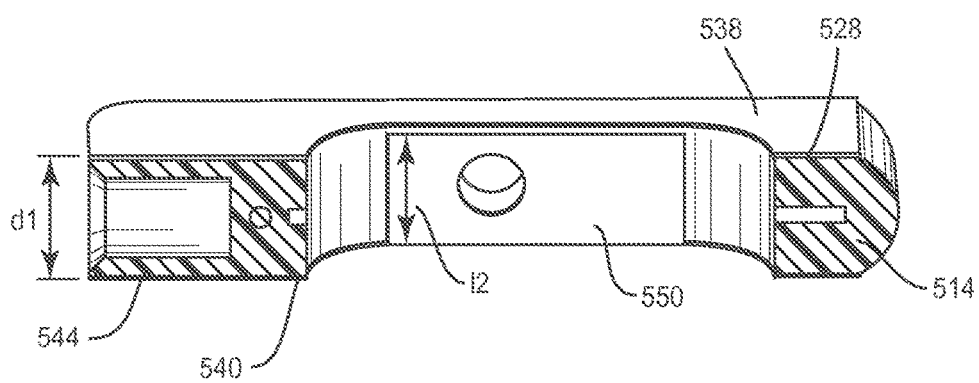
FIG. 13 is a cross section view of the components shown in FIG. 12.
Figure 14:
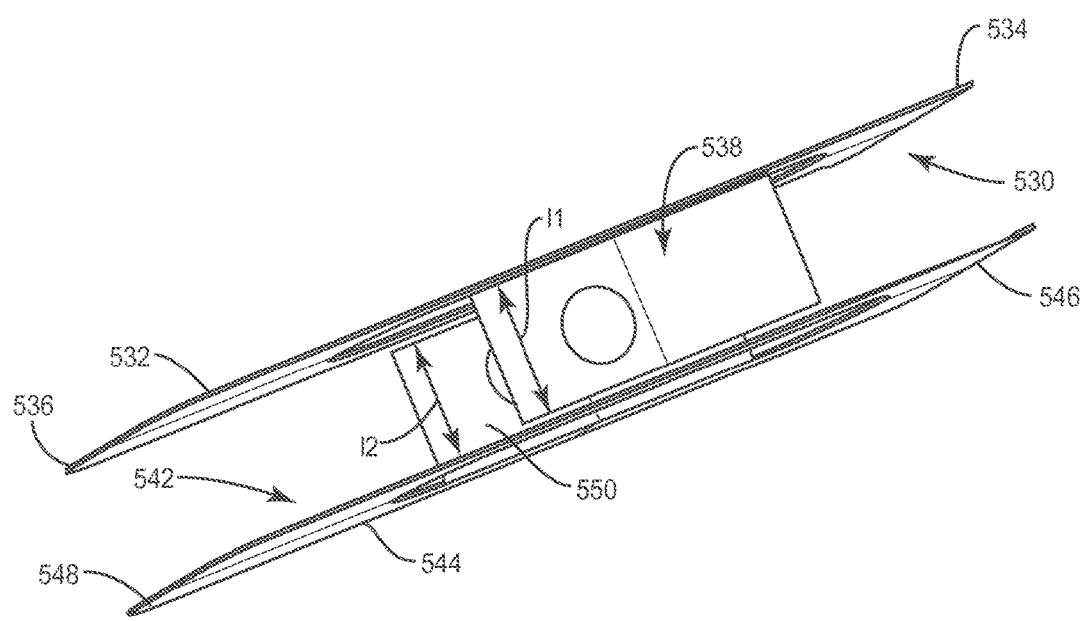
FIG. 14 is perspective view of components of the surgical system shown in FIG. 12.

In one embodiment, as shown in FIGS. 12-14, surgical system 10, similar to the systems and methods described herein, includes an interbody implant 512, similar to interbody implant 12, described herein. Interbody implant 512 includes an interbody cage 514, similar to cage 14 described herein, which extends between a leading end 518 and an insertion end 520. End 520 includes a surface 522 that defines a cavity 524 configured for engagement with an insertion tool (not shown). Interbody implant 512 includes an opening 526, similar to opening 26 described herein. Opening 526 includes a depth d1.

Cage 514 includes a surface 528. An electrode, such as, for example, a frame 530 is mounted with cage 514 and attached with surface 528. Frame 530 comprises an anode electrode of electronic components and/or circuitry of spinal implant system 10 that is connected with interbody implant 512. Frame 530 includes an endplate 532, which extends between an end 534 and an end 536. End 534 is configured for engagement with leading end 518 of cage 514, as described herein. End 536 is configured for engagement with insertion end 520 of cage 514, as described herein. Endplate 532 includes a flange 538. Flange 538 includes a length l1. Flange 538 extends into opening 526 in a direction towards a frame 542, as described herein. Length l1 is less than depth d1 such that frame 530 is electrically isolated from frame 542, as described herein.

Frame 530 mates with cage 514, similar to that described herein, and/or a circuit board assembly of interbody implant 512, similar to circuit board assembly 80 described herein. Frame 530 includes an electrically conductive material. In some embodiments, frame 530 includes a coating fabricated from titanium. In some embodiments, the electrically conductive material of frame 530 may be fabricated from various materials, such as, for example, metals as described herein, electrolytes, superconductors, semi-conductors, plasmas and non-metallic conductors such as graphite and conductive polymers.

Direct electric current is supplied to frame 530, similar to that described herein, and is configured to conduct electric current through tissue, an agent, interstitial tissue and/or fluids disposed adjacent cage 514 and/or within opening 526. Frame 530 conducts the electric current through cage 514 and to frame 542, as described herein, in a configuration to generate a selected electric field in, around, about, through and/or adjacent to interbody implant 512 to selectively stimulate bone growth in, around, about, through and/or adjacent interbody implant 512.

Cage 514 includes a surface 540. An electrode, such as, for example, a frame 542 is mounted with cage 514 and attached with surface 540. Frame 542 comprises a cathode electrode of electronic components and/or circuitry of spinal implant system 10 that is connected with interbody implant 512. Frame 542 includes an endplate 544, which extends between an end 546 and an end 548. End 546 is configured for engagement with leading end 518 of cage 514, as described herein. End 548 is configured for engagement with insertion end 520 of cage 514, as described herein. Endplate 544 includes a flange 550. Range 550 includes a length l2. Range 550 extends into opening 526 in a direction towards frame 530. Length l2 is less than depth d1 such that frame 542 is electrically isolated from frame 530.

Frame 542 mates with cage 514 and/or the circuit board assembly of interbody implant 512. Frame 542 includes an electrically conductive material. In some embodiments, frame 542 includes a coating fabricated from titanium. In some embodiments, the electrically conductive material of frame 542 may be fabricated from various materials, such as, for example, metals as described herein, electrolytes, superconductors, semi-conductors, plasmas and non-metallic conductors such as graphite and conductive polymers.

Frame 542 is configured to conduct direct electric current through tissue, an agent, interstitial tissue and/or fluids disposed adjacent cage 514 and/or within opening 526. Frame 542 conducts the electric current through cage 514 and from frame 530, as described herein, in a galvanic coupling to generate a selected electric field, similar to electric field EF described herein, in, around, about, through and/or adjacent to interbody implant 512 to selectively stimulate bone growth in, around, about, through and/or adjacent interbody implant 512.

In some embodiments, interbody implant 512 includes electronic components, such as, for example, a printed circuit board assembly, similar to printed circuit board assembly 80 described herein, which includes one or more components for delivering electric current to the electrodes, powering interbody implant 512 and/or detecting/sensing diagnostics. In some embodiments, the printed circuit board assembly of interbody implant 512 is connected with and/or includes circuitry and one or more integrated circuits or micro-electronic chips for delivering electric current to the electrodes, powering interbody implant 512 and/or detecting/sensing diagnostics, similar to that described herein. In some embodiments, the printed circuit board assembly of interbody implant 512 includes integrated circuits that can remotely communicate with electronic components of spinal implant system 10 disposed outside or external to a body of a patient, similar to that described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   an implant body including a first endplate and a second endplate the first endplate including a vertebral engaging surface defining a first electrode, the second endplate including a vertebral engaging surface defining a second electrode, the first and second electrodes being configured to conduct an electric current to stimulate tissue growth adjacent the implant body, a distance between the vertebral engaging surfaces defining a maximum height of the implant body,
   wherein the first electrode comprises a titanium coated anode and the second electrode comprises a titanium coated cathode.

2. A spinal implant as recited in claim 1, wherein the implant body defines a cavity and the electrodes are selectively configured with the implant body to generate an electric field adjacent the implant body to selectively stimulate tissue growth adjacent the implant body and within the cavity.

3. A spinal implant as recited in claim 1, wherein the electrodes are selectively configured with the implant body to generate an elliptical electric field adjacent the implant body to selectively stimulate tissue growth adjacent the implant body.

4. A spinal implant as recited in claim 1, wherein the first electrode comprises at least two anodes and the second electrode comprises at least two cathodes, the electrodes being selectively configured with the implant body to generate an electric field adjacent the implant body to selectively stimulate tissue growth adjacent the implant body.

5. A spinal implant as recited in claim 1, wherein the implant body includes at least one diagnostic sensor.

6. A spinal implant as recited in claim 1, wherein the implant body includes at least one diagnostic sensor that detects impedance between the electrodes.

7. A spinal implant as recited in claim 1, wherein the implant body communicates with at least one remote power source.

8. A spinal implant as recited in claim 7, wherein the implant body includes an integrated circuit for communicating with the at least one remote power source.

9. A spinal implant as recited in claim 1, further comprising a substrate including at least one electronic component that is electrically connected to one or more of the first and second electrodes.

10. A spinal implant as recited in claim 1, wherein the implant body is molded with the first and second electrodes.

11. A spinal implant as recited in claim 1, wherein the vertebral engaging surfaces each include a plurality of teeth.

12. A spinal implant as recited in claim 1, further comprising a printed circuit board assembly positioned between the endplates.

13. A spinal implant as recited in claim 12, wherein the printed circuit board assembly comprises a power harvesting integrated circuit that enables the implant body to establish radio communication at a short distance to supply power to charge the printed circuit board assembly.

14. A spinal implant as recited in claim 12, wherein the printed circuit board assembly comprises an antenna configured to convert magnetic fields into energy such that the endplates conduct electric current to selectively stimulate tissue growth adjacent the implant body.

15. A spinal implant comprising:
an interbody cage including a first surface, a second surface and an inner surface that defines a cavity configured for disposal of bone graft, the first surface defining a titanium coated anode, the second surface defining a titanium coated cathode, a distance between the surfaces defining a maximum height of the interbody cage; and
a substrate including at least one electronic component that is electrically connected to the anode and the cathode, the anode and the cathode conducting an electric current to stimulate tissue growth adjacent the interbody cage.

16. A spinal implant comprising:
an implant body including a first end having a blunt tip and an opposite second end defining a cavity configured for engagement with a surgical instrument, the implant body including opposite top and bottom surfaces and a printed circuit board assembly positioned between the top and bottom surfaces, the cavity being positioned between the top and bottom surfaces;
a first endplate positioned in a recess of the top surface and including a vertebral engaging surface defining a first electrode; and
a second endplate positioned in a recess of the bottom surface such that the second endplate is spaced apart from the first endplate by the implant body, the second endplate including a vertebral engaging surface defining a second electrode, the first and second electrodes being configured to conduct an electric current to stimulate tissue growth adjacent the implant body,
wherein the spinal implant comprises an opening configured for disposal of an agent, the opening extending continuously through the implant body and the endplates.

17. A spinal implant as recited in claim 16, wherein the printed circuit board assembly comprises:
a power harvesting integrated circuit that enables the implant body to establish radio communication at a short distance to supply power to charge the printed circuit board assembly; and
an antenna configured to convert magnetic fields into energy such that the endplates conduct electric current to selectively stimulate tissue growth adjacent the implant body.

* * * * *